United States Patent [19]
Hodson et al.

[11] Patent Number: 5,655,523
[45] Date of Patent: Aug. 12, 1997

[54] DRY POWDER INHALATION DEVICE HAVING DEAGGLOMERATION/ AEROSOLIZATION STRUCTURE RESPONSIVE TO PATIENT INHALATION

[75] Inventors: Peter David Hodson, Trowell Park; David Keith Smith, Loughborough; Anthony Charles Lammond Wass, Duddington, all of Great Britain

[73] Assignee: Minnesota Mining and Manufacturing Company, St. Paul, Minn.

[21] Appl. No.: 446,446

[22] Filed: May 22, 1995

Related U.S. Application Data

[63] Continuation of Ser. No. 167,730, filed as PCT/GB90/00670 Apr. 10, 1990.

[30] Foreign Application Priority Data

Apr. 28, 1989 [GB] United Kingdom ............ 8909891
Jan. 5, 1990 [GB] United Kingdom ............ 9000261

[51] Int. Cl.$^6$ ............ A61M 15/00; A61M 16/00; B05D 7/14; B05D 83/06
[52] U.S. Cl. ............ 128/315; 128/203.12; 128/203.21
[58] Field of Search ............ 128/203.12, 203.15, 128/200.14, 200.16, 200.17, 200.21, 200.22, 200.24, 203.21, 203.23, 204.13; 604/56

[56] References Cited

U.S. PATENT DOCUMENTS

| | | |
|---|---|---|
| 3,777,742 | 12/1973 | Aumiller et al. . |
| 3,915,165 | 10/1975 | Rambosek et al. . |
| 3,948,264 | 4/1976 | Wilke et al. . |
| 3,971,377 | 7/1976 | Damani . |
| 4,109,656 | 8/1978 | Goethel et al. . |
| 4,147,166 | 4/1979 | Hansen . |
| 4,446,862 | 5/1984 | Baum et al. . |
| 4,735,358 | 4/1988 | Morita et al. . |
| 5,031,610 | 7/1991 | Armstrong et al. . |
| 5,119,806 | 6/1992 | Palson et al. . |

FOREIGN PATENT DOCUMENTS

| | | |
|---|---|---|
| 224335 | 6/1987 | European Pat. Off. . |
| 2516387 | 5/1983 | France . |
| 2598918 | 11/1987 | France . |
| 2831553 | 1/1980 | Germany . |
| 2837040 | 2/1980 | Germany . |
| 898649 | 6/1962 | United Kingdom . |
| 1479283 | 7/1977 | United Kingdom . |
| 2061735 | 5/1981 | United Kingdom . |
| 2108390 | 5/1983 | United Kingdom . |
| 2122903 | 1/1984 | United Kingdom . |
| 2166957 | 5/1986 | United Kingdom . |
| 85/01880 | 5/1985 | WIPO . |
| 90/13328 | 11/1990 | WIPO . |

*Primary Examiner*—Kimberly L. Asher
*Attorney, Agent, or Firm*—Gary L. Griswold; Walter N. Kirn; Ted K. Ringsred

[57] ABSTRACT

An inhalation device for dry powder containing a chamber capable of receiving a dose of powdered medicament. The chamber is in communication with a patient port in the form of a mouthpiece or nasal adapter. The inhalation device also contains a deagglomeration/aerosolization apparatus capable of deagglomerating and/or aerosolizing a dose of powdered medicament and is operable by a patient-independent energy output source. The inhalation device further includes detection apparatus that ascertains patient inspiration through the patient port, and a control apparatus that actuates the deagglomeration/aerosolization apparatus in response to detection of patient inspiration.

15 Claims, 8 Drawing Sheets

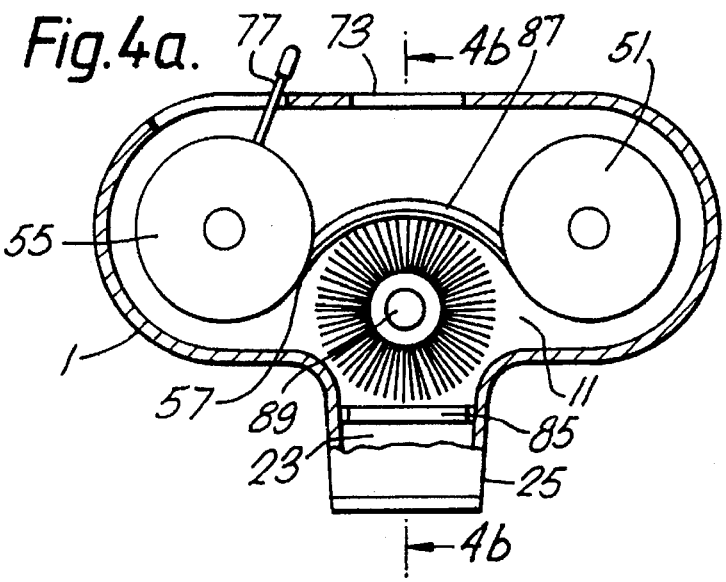
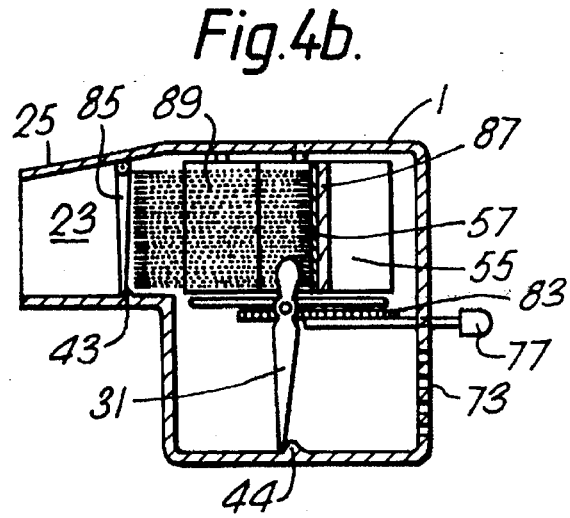
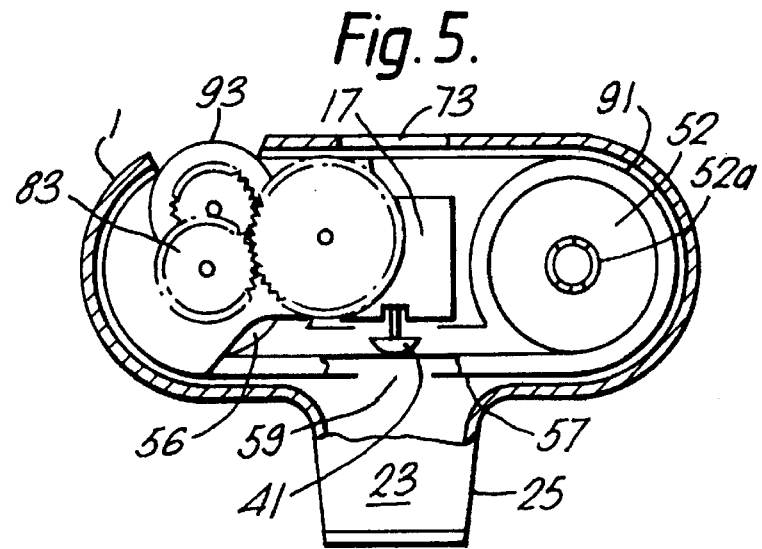

DRY POWDER INHALATION DEVICE HAVING DEAGGLOMERATION/ AEROSOLIZATION STRUCTURE RESPONSIVE TO PATIENT INHALATION

This application is a continuation of U.S. application Ser. No. 07/167,730, which was a 371 of PCT/GB90/00670, filed Apr. 10, 1990.

FIELD OF THE INVENTION

This invention relates to dry powder inhalation devices and in particular to an inhalation device in which a dose of powdered medicament is aerosolized for inhalation by a patient, which aerosolization is independent of the patient's inspiratory effort.

BACKGROUND

Asthma and other respiratory diseases have long been treated by the inhalation of appropriate medicament. For many years the two most widely used and convenient choices of treatment have been the inhalation of medicament from a drug solution or suspension in a metered dose pressurized inhaler (MDI), or inhalation of powdered drug generally admixed with an excipient, from a dry powder inhaler (DPI). With growing concern being voiced over the strong link between depletion of the earth's ozone layer and chlorofluorocarbon emissions, the use of these materials in pressurized inhalers is being questioned and interest in DPI systems has been stimulated.

Known single and multiple dose dry powder devices use either individual pre-measured doses, such as capsules containing medicament which is inserted into the device prior to use, or incorporate a bulk powder reservoir from which successive quantities of medicament are transferred to a dispensing chamber. Whilst it is desirable to utilize the action of a patient's breathing both to aerosolize powdered drug in the device and inhale the powder, thereby overcoming the coordination problems necessary to synchronize inspiration with means for medicament release, the efficiency of aerosolizing the particles of powder is dependent upon the patient's inspiratory effort and in some cases a patient having breathing problems, e.g., during an asthmatic attack, may have insufficient inspiratory effort to aerosolize and inhale the required dose of medicament at a time when the patient has the greatest need for drug.

Agglomeration is caused by particles of medicament adhering together in a semi-rigid mass, and requires an increased inspiratory effort by the patient to break up and entrain drug particles into the air stream. If the patient is unable to provide sufficient inspiratory effort the extent of drug penetration into the lower airways of the lung will be reduced. Larger agglomerated drug particles (approximately 10 µm or greater) which result from inefficient aerosolization are not stably entrained into the patient's air stream and prematurely deposit in the mouth/throat region which may lead to unwanted systemic side effects, especially when potent drugs are administered.

Some inhalation devices have attempted to solve the problems attributable to agglomeration and medicament release, for example, U.S. Pat. Nos. 3,948,264, 3,971,377 and 4,147,166 disclose inhalers for dispensing medicament in the form of a dry powder contained in a rupturable capsule. After breaching the capsule the patient is required to externally manipulate means for operating a power source to provide the input of energy, necessary to release medicament from the capsule, while simultaneously inhaling through the device.

U.S. Pat. No. 3,948,264 discloses the use of a battery powered solenoid buzzer to vibrate the capsule effecting medicament release.

U.S. Pat. No. 3,971,377 discloses the use of a propeller to generate an airflow effecting medicament release. The power source comprises an electric motor, battery and external switch combination or a threaded plunger arrangement.

U.S. Pat. No. 4,147,166 discloses the use of an impeller to generate sufficient air turbulence to effect medicament release. The power source comprises a battery driven motor, a compressed gas power turbine or a hand power driven differential gear.

These devices are unsatisfactory as they permit deagglomeration/aerosolization to take place for an uncontrolled period of time prior to inspiration, additionally, the patient may forget to activate the device before inhalation. Thus, the size and effectiveness of the dose received by the patient's respiratory system may vary between individual patients and/or between individual occasions of use.

British Patent Specification Nos. 898649 and 1479283 disclose dry powder inhalers comprising either a manually squeezed bellows or bulb to generate greater than atmospheric pressure in an air reservoir. Inspiration by the patient operates a valve mechanism which discharges the compressed air into a chamber containing a dry powder capsule and hence into the patient's respiratory system. However, the aforementioned devices remain patient dependent even though the energy used to aerosolize and deagglomerate the powder is not supplied by the patient's inspiratory effort. The degree of pressure exerted upon the bulb or bellows will affect the energy supplied by the compressed air which in turn will effect the nature of the dose of powdered drugs inhaled. For example, old, arthritic or very young patients may exert considerably less pressure than a more able individual. Similarly those individuals afflicted with an asthma attack find the devices cumbersome and/or complicated at a time when they are under severe stress. Furthermore, in each case the patient must remember to operate the squeezy bulb or bellows prior to inhaling, and must continue to exert pressure on these means during inhalation.

SUMMARY OF THE INVENTION

According to the present invention there is provided a dry powder inhaler comprising a housing defining a chamber for receiving a dose of powdered medicament in communication with a patient port in the form of a mouthpiece or nasal adapter, the inhaler additionally comprising;

deagglomeration/aerosolization means to cause or assist aerosolization and/or assist deagglomeration of said dose of powdered medicament, which means is operable by a patient-independent energy output source, detection means to detect patient inspiration through the patient port, and, control means to actuate said deagglomeration/ aerosolization means in response to detection of patient inspiration by said detecting means.

The present invention provides a dry powder inhaler capable of dispensing reproducible doses of powdered medicament in terms of both dose size and state of deagglomeration, by offering performance independent of a patient's inspiratory effort, manual dexterity, physical strength or ability to coordinate separate movements such as breathing and starting to squeeze, or breathing and pressing a button or lever during administration of the medicament.

The inhaler is made patient independent by the incorporation of a patient-independent energy output source for deagglomeration/aerosolization of medicament and a breath actuation mechanism, responsive to inspiratory flow, able to synchronize medicament release with inhalation. Thus, in order to receive a dose of medicament, the patient simply inhales through the mouthpiece. The detection means detects the patient's inspiration and triggers the deagglomeration/aerosolization means which operates to ensure efficient aerosolization of the medicament in the air stream. The energy for operation of the deagglomeration/aerolization means during inspiration is independent of the patient's inspiratory effort and does not require any manual effort by the patient during the administration of the medicament.

The inhalation devices of the invention may be of either single dose format, requiring insertion of a new dose after each successive use, or multiple dose format whereby the device contains a plurality of such doses. Single medicament doses are generally enclosed in a rupturable capsule, which is normally inserted into the device on a need to use basis. Typically, the patient will carry a plurality of such capsules in a pop-out tab about their person. Multiple dose devices may also utilize capsules but more commonly include a medicament powder reservoir and a powder transfer member for delivering a dose of medicament to the chamber.

Normally the capsules are formed of gelatin, although any suitable material which is both inert to the drug contained within and able to be satisfactorily punctured or otherwise split, may be used. The capsule may be manually opened or ruptured by the patient prior to insertion into the device, or, the sealed capsule ruptured during or after insertion into the device.

In one embodiment the capsule is securely mounted in an enclosure within the aerosolization chamber and punctured in situ by one or more retractable piercing members, typically spring biased and operated by opening of the mouthpiece prior to inhalation.

Alternatively, a multiple dose inhaler may include a bulk powder reservoir and a length or area of a suitable material forming part or all of a powder transfer member, which member moves past or through a storage chamber containing the powdered medicament in such a way that a controlled quantity of the powder is transferred to the surface of the material.

The material and its powder coating then pass into the aerosolization-chamber of the device where some physical force is applied to the material in order to release a fixed proportion of the powder as an aerosol suitable for inhalation.

The powder transfer member preferably comprises a material of suitable surface characteristics to allow its uniform coating with powder. The member may incorporate a number of sub-members, for example, for purposes of support and conferring rigidity, or may be composed solely of the transfer material itself. Examples of materials which may be suitable, include non-woven fibrous materials, shaped filament materials such as, the products sold under the trademarks 'Scotchmate' or 'Dual-Lock' commercially available from Minnesota Mining and Manufacturing Company; microporous materials, microgrooved polymer materials or structured surface materials having small surface grooves or recesses formed in their surface of a typical size of <500 μm deep and of 500 μm or less in at least one other dimension. The physical form of this powder transfer material would preferably be a tape or disk, although other forms may also be used, for example, string or cord, or simply an area of material in some shape such as a rectangle.

The nature of the movement of the material, between the powder storage chamber and the region of the device where aerosolization takes place, is related to its physical form. For example, a tape, string or cord may be used, preferably to give linear transport through or past the storage chamber, whilst a disk may be rotated, preferably such that a given part of the disk is in the storage chamber and a second part in the aerosolization chamber at any one time. A defined area of powder transfer material is then rotated from the filling station to the aerosolization chamber. Any particular part of the surface area of the powder transfer material may or may not be used more than once.

The loading of the transfer material with powder from the storage chamber may be by any suitable means. For example, the transfer material may move through the powder, or may pass underneath it or over it. The transfer member may itself form one boundary of the powder storage chamber. The powder transfer material may pass over or between brushes, rollers, scrapers, etc., or other dosing means, in order to control or modify the quantity of powder coated onto it. For example, microgrooved material could be uniformly coated with powder (and the dosage thus accurately controlled) by scraping powder into the grooves on its surface in order to fill them. For other materials, dosage determination may be effected by careful control of the transfer material/powder reservoir interface parameters, e.g., by the control of the forces under the influence of which they are brought into contact.

An example of an arrangement suitable for use with the devices of the invention is disclosed in European Patent Application No. 69715 wherein the powder reservoir comprises a storage chamber and the transfer member comprises a horizontally oriented perforated membrane mounted on a rotatable maneuvering unit. Thus, the storage chamber and membrane are displacably arranged in relation to one another between a first position, in which medicament is introduced into the perforations in at least a part of the area of the membrane, and a second position, in which the area of the membrane so loaded is rotatably displaced into the aerosolization chamber prior to input of deagglomeration/aerosolization energy.

Problems are sometimes further caused by the necessity to provide a sufficient quantity of powder (e.g., several hundred μg) to overcome problems associated with the accurate transferral of measured small quantities of drug into a capsule or onto a transfer member. Thus, with potent drugs, the medicament is normally compounded with an excipient, such as lactose powder, to increase the quantity of powder to be measured. Excipients are undesirable as they are generally of too great a size to be themselves inhaled, and yet they may retain adherent drug particles which thus get deposited in the mouth and throat. In addition responsible for dental caries. Therefore, in a most preferred embodiment, the medicament source comprises a pre-loaded elongate carrier, as disclosed in British Patent Application No. 8909891 filed on the 28th Apr. 1989 and PCT application No. U.S. 90/02412 of even date.

Devices utilizing an elongate carrier provide a simple, effective dry powder inhaler which is capable of delivering multiple, uniform doses of a medicament to a patient. The device is simple to operate and does not require the patient to insert capsules of medicament or rely upon a separate reservoir of medicament in order to load the device for use. The medicament is preloaded on an elongate carrier, sections of which are passed sequentially into the chamber for dispensing the medicament. The elongate carrier may be conveniently loaded on a spool (in a similar manner to a photographic film) or in a cassette (in a similar manner to an audio cassette). The elongate carrier may have any ratio of length: width but is preferably greater than 5:1, more preferably greater than 10:1 and more preferably between 100:1 and 1000:1.

The preloaded elongate carrier can take a variety of forms, but preferably is a tape, web, belt or cord. The powdered medicament may be retained on the carrier by electrostatic attraction, van der Waals forces, physical attraction, mechanical binding, wedging or by a cover layer or an overlying layer of the same carrier when the carrier is wound etc. One or more surfaces of the carrier and optionally the interior of the carrier may be configured to assist in retaining the particles of powder.

The carrier may be constructed from one or more of a wide range of natural and synthetic materials e.g. polyethylene, polypropylene, polyester, polytetrafluoroethylene or a copolymer thereof and cellulose. The materials may be in the form of non-woven fibrous materials, loose weave materials or fabrics, materials having a surface pile, films, microporous materials, microgrooved materials, cords of twisted fibres, or any material or composite of more than one material having small surface grooves, recesses, interstices, apertures or embossed surface structures having a typical size of <500 µm in either depth or height and of greater than 0.1 µm in at least one other dimension in order to retain the particles of powder.

A microgrooved material preferably comprises a tape, web or belt with one or more grooves of width 10 to 500 µm at the carrier surface and a depth of 10 to 500 µm, but the grooves may generally have dimensions at least an order of magnitude larger than the largest particle. The microgrooves may be filled partially, or completely, the latter facilitating a means of dosage control if the material is loaded under uniform conditions. The microgrooves need not be continuous or straight and may run in one or two dimensions.

A microporous material preferably comprises a tape, web or belt having pores of diameter 0.1 to 100 µm which may be randomly orientated. At least a portion of the pores must be on the exterior surface. A preferred method of pore formation utilizes solvent extraction of oil droplets dispersed in a film of carrier material.

A further embodiment of a microporous material is produced by a laser drilling process and comprises a tape, web or belt having pores of diameter 1 to 100 µm, preferably 20 to 50 µm, in at least one surface.

A non-woven material may be of any suitable format, but is preferably in the form of a tape, web or belt. It may contain any type and form of fibers, although fibers of 0.1 µm to 100 µm diameter are preferred and most preferably 5 to 20 µm diameter. Fibers may be of any appropriate length but preferably 1 to 100 mm. Formation of the non-woven material may be any suitable method, for example, combing or carding, deposition of fibers from a transport gas or fluid, or the extrusion and blowing of microfibers. Bonding, e.g. by thermal fusion, of the fibers over at least part of the area of the material may be carried out to increase the mechanical strength of the material. Such bonding may be most conveniently situated at the edges of the tape or web and may be conveniently formed as part of a process of slitting the tape, e.g., by a thermal or laser slitting means. The material may also be perforated or embossed and may optionally be air permeable.

The non-woven material may use a mixture of fiber compositions or forms. In one preferred embodiment, bicomponent fibers, with a readily fusible outer component, are used. Such fibers are capable of ready inter-bonding to prevent, or minimize fiber shedding. In another preferred embodiment, spun-bonded fibers are used to achieve the same objective by taking advantage of their longer fiber length. In a third embodiment, continuous reinforcing filaments may lie in the plane of the material, so providing fiber anchorage and conferring additional mechanical strength to the material. In a fourth embodiment, paper type non-woven materials formed by deposition of fibers from a liquid may be used, as they may possess additional strength compared to other materials and may lead to reduced fiber shedding, due to increased fiber entanglement.

The tape, web or belt may contain reinforcing threads in the plane of the material and/or a backing layer e.g. a metal foil such as aluminium, or a polymer film or a combination thereof. A metallized backing layer is advantageous when the carrier is stored as a roll because it imparts a conducting surface, which may reduce transfer of medicament from the coated surface to the uncoated surfaces. The backing layer may have perforations to allow for passage of an airflow through the carrier material proper.

The carrier may be loaded by the brushing, scraping or smearing of powdered medicament onto the carrier surface.

Alternatively the carrier may be loaded by evaporation from a suspension of medicament, by precipitation from a solution of medicament or by deposition from an aerosol for example by spraying, impaction, impingement, diffusion or by electrostatic or van der Waals attractions. For example, the medicament particles may be given an intentional electrical charge immediately prior to loading. The technique of charged aerosol deposition may be complimented by the use of a carrier with an inherent electrostatic charge. Ideally, the carrier should be an insulator such as polytetrafluoroethylene capable of retaining the charge, alternatively the carrier may contain an artificial charge due to the presence of electrets. Generally, the choice of loading technique will be governed by the properties of the carrier material employed.

Masks stencils etc. may be employed during coating, in order to allow the coating of discrete areas of carrier medium with individual doses. Patterned deposition of the medicament may be used to prevent contact between drug and any ink markings on tape.

A preferred carrier for use in this invention is disclosed and claimed in U.S. Pat. No. 5,192,548 incorporated herein by reference. That Patent Application discloses a flexible sheet material comprising a plurality of discrete depressions in at least one surface thereof, each of the depressions having a depth of about 5 to 500 μm, but less than the thickness of the sheet material, and an opening at the surface of the sheet material of about 10 to 500 μm across, a substantial number of the depressions being at least partially filled, preferably at least 75% filled, with micronized medicament, and the area of the surface of the sheet material between the depressions being substantially free of micronized medicament.

The flexible sheet material may comprise a substantially regular array of depressions or microdimples formed in the top surface of a layer of polymeric material. The depressions are generally truncated cones, but may alternatively be of any suitable configuration for holding micronized medicament including generally truncated pyramids, partial hemispheres and tetrahedrons and other geometric configurations or non-geometric configurations. Presently preferred depressions have a sidewall angle of about 15° to 20° to the vertical. The array of depressions may take any form or pattern and need not be regular (i.e., the array may be irregular in appearance).

The depressions generally have a depth of about 5 to 500 μm and an opening at the surface of the sheet material of about 10 to 500 μm across with respect to the major axis of the opening. In the case of the depressions having generally circular openings such as truncated cones or partial hemispheres, for example, the major axis discussed above is, in fact, the diameter of the circular opening. Preferred depressions have a depth of about 10 to 100 µm and an opening (e.g., diameter in the case of truncated cones or partial hemispheres or the like) at the surface of the sheet material of about 50 to 200 µm. The depressions generally will be spaced about 20 to 200 µm, preferably about 50 to 200 µm, from one another. Preferably the depressions will number from about 500 to 15,000 per $cm^2$ of the sheet material. The volume of each depression and the spacing or number of the depressions will depend upon the potency of the medicament and the area of the sheet material intended to represent a single dose of the medicament. Preferably, the sheet material will have a substantially uniform depression volume per unit area.

The sheet material may further comprise a support layer, e.g., of paper. The layer of polymeric material may be laminated or melt-bonded to or extruded onto the support layer. Other support layers may be formed of non-wovens or polymers such as polyester.

The layer of polymeric material may comprise any suitable polymer such as polyethylene, polypropylene, polyester, polytetrafluoroethylene and cellulose. Polyethylene is preferred. The layer of polymeric material will be typically about 25 to 100 µm in thickness.

The sheet material may be formed of a single material such as polypropylene. The support layer is not required in such an embodiment since the sheet material even without the support layer will exhibit sufficient integrity and durability.

A preferred sheet material is prepared using polyethylene-coated kraft paper available from Schoeller Company. The depressions have a depth such that they do not form pores extending through the entire thickness of the sheet material.

The top surface of the sheet material is generally coated with micronized drugs to at least partially fill the depressions followed by general removal of excess drug from the top surface of the sheet material in the areas of the top surface between the depressions, e.g., by scraping optionally followed by rolling between silicone pads.

As the packing density of the micronized medicament in the depressions may have influence on the form and amount of medicament released from the sheet material during the aerosolization process, care should be taken to assure that the packing density remains substantially uniform during the coating process.

The opening and depth dimensions and the spacing of the depressions influence how much micronized medicament the sheet material can carry per unit area for a given degree of compression of the medicament during loading or coating. Further, depression depth may influence the degree to which medicament is released from the sheet material and its relative state of agglomeration or unagglomeration. Using salbutamol sulfate with a mean particle size of 1.7 μm and for single impactions of strength appropriate to an inhaler on areas of about 2 to 10 $cm^2$ of sheet material, the following was observed. The percentage of medicament retained on the sheet material or tape decreases as depression depth increases, this being about 95% at 14 μm, about 60% at 28 μm and about 35% at 45 μm. Further, the respirable fraction (i.e., the percentage of drug which is in particles of aerodynamic diameter of equal to or less than about 6.4 μm) similarly decreases as depression depth increases, this being about 65% at 14 μm, about 30% at 28 μm and about 10% at 37 μm. These two trends result in the proportion of total medicament released in particles of respirable size remaining generally similar for the depression depths studied (this being about 5 to 15% of total medicament).

Depressions may be formed in the sheet material by any suitable technique such as micro-imprinting using a photolithographically-patterned magnesium alloy plate or other micro-machined plate. Other conventional techniques which may be used are optical imaging or laser imaging.

As an illustrative example a sheet material has been prepared using a photolithographically produced etched magnesium alloy master plate having an array of pyramidal-shaped protuberances numbering about 1550 per $cm^2$ wound about a steel roller. The roller was heated to about 225° F. using oil. The polyethylene surface of polyethylene-coated kraft paper (commercially available from Schoeller Company) was pressed against the surface with a rubber or steel nip roll, also heated with oil and hydraulically pressurized against the patterned roll.

It is preferred that the medicament employed exhibit a potency which permits a single dose to be loaded onto the sheet material in an area of less than about 25 $cm^2$ and preferably less than about 5 $cm^2$. More preferred is a sheet material containing a drug in such a manner and of such a type that between 0.25 and 2.25 $cm^2$ most preferably between 0.5 and 2.0 $cm^2$, of the sheet material will contain a single dose. Stated differently, given that a sheet material of the invention may conveniently carry between about 10 and 150 μg of medicament per $cm^2$, the potency of the medicament will preferably be such that a single dose may be carried on the above stated 0.25 to 2.25 $cm^2$ of sheet material.

The format of the carrier in the most preferred embodiment is a tape. The nature of the carrier dictates the method of transport between storage means and the chamber where aerosolization takes place. In a preferred embodiment, storage of preloaded carrier is effected by winding on a spool which is contained within a cassette. Use of a tape web or belt allows other conformations to be imparted to the stored carrier by folding, for example, as a concertina conformation which has the advantage that the medicament bearing surfaces are in association and thereby prevent net transfer of medicament during storage. Each fold may define a unit dose of medicament. Folding along the longitudinal axis of the tape, referred to as hybrid folding, may also reduce unwanted net transfer of medicament. Cord or string may conveniently be stored as a coil.

The device includes means for advancing the elongate carrier through the chamber to sequentially expose areas of the carrier for release of medicament during inhalation by the patient. The means for advancement may take a variety of forms depending upon the type of elongate carrier and whether the exposed areas of carrier are to be retained within the device. For example, tapes webs and belts may include a series of apertures which are engaged by one or more sprocketed guide wheels or rollers in a similar manner to a camera or printer. Alternatively, or in addition, the carrier may be wound on a take-up spool, rotation of the spool directly or via a drive belt causing the carrier to advance. The device may also include means for tensioning or otherwise maintaining the exposed area of the carrier within the chamber during inhalation by the patient.

The elongate carrier may be advanced into the chamber prior to inhalation by the patient preferably or the carrier may be advanced into the aerosolization chamber during inhalation to protect the powdered medicament from premature exposure. For example in one embodiment of the inhaler an unexposed area of carrier is rapidly advanced into the chamber upon actuation, and is rapidly decelerated or brought to an abrupt halt and preferably is impacted thereby imparting sufficient energy to the medicament particles to effect their displacement from the carrier into the air stream.

In the preferred embodiment of the invention the elongate carrier is stored in a cassette both before and after exposure. The cassette may comprise one or preferably two spools together with idlers or other rollers and include an exposure frame positioned within the chamber, through which the carrier is advanced. The cassette may be removable to allow the device to be recharged with a new cassette. However, it is not essential for the exposed areas of the carrier to be retained within the device and spent carrier may be advanced to the exterior of the device through a slot in the housing whereupon disposal may be effected by the patient, optionally with the aid of a cutting edge. This arrangement is particularly suitable for a tape carrier which has transverse perforations to facilitate tearing off spent carrier.

The predetermined area of carrier to be exposed in the chamber may be from 0.1 to 20 $cm^2$ and preferably from 2 to 3 $cm^2$. The medicament may coat one of more surfaces of the carrier and/or be entrapped within interstices in the carrier to allow a dose of 5 μg to 1 mg to be entrained within the airflow produced at inhalation. It is not essential that all of the drug be so entrained within the airflow, providing the amount of drug released from the predetermined area is reproducible on consecutive use.

The device may additionally include means to indicate one or more of a variety of parameters, such as, readiness for use, contents remaining, type of drug etc.

The indicator may just provide warning of the near-exhaustion of the medicament supply or it may provide more detailed information, such as the sequential number of the dose or the number of doses remaining. The indicator may additionally provide information to the date of manufacture or date of expiry of the medicament, as additional examples. For treatment intended to be taken regularly at set times, the indicator may display the intended day, date and time of administration. The information displayed by the indicator may conveniently be marked on the tape or tape covering by any appropriate method whether involving printing, indenting etc. The area of tape in the indicator need not be that used to release the drug at that time.

Dry powder inhalation devices comprising an elongate carrier may possess numerous advantages over the prior art devices. For example:

1. An inhaler with dosage control by the removal of powder from a fixed area of uniformly coated tape shows improved dose uniformity and respirable fraction uniformity over prior art devices. High respirable fractions are desirable because they allow a high proportion of the drug to be inhaled into the lungs to provide therapeutic benefit, and reduce the proportion of the drug causing unwanted systemic side-effects following swallowing from the mouth and throat region.

2. The inhaler allows the accurate administration of smaller quantities of undiluted potent drugs (typically below 200 μg) such as corticosterioids, than is currently possible. This removes the problems associated with the use of excipients.

3. The storage of pure, powdered medicament on the surface of a tape lends itself to dosage adjustment or the use of different drugs with the minimum of effort and without reformulation work.

4. The inhaler is suitable for use with a wide variety of different medicaments.

5. By controlling the tape or web dimensions, a precise number of doses for inhalation can be stored in the inhaler.

6. The tape can be marked to allow the inhaler to register the exact number of doses remaining, or alternatively some counter mechanism can be driven by the tape advance mechanism.

7. The amount of drug inhaled and the degree of particle deagglomeration are independent of the patient's inspiratory effort overcoming the requirement for hand/lung coordination, while at the same time, providing a consistent dose each time for all patients, irrespective of lung function.

8. As aerosolization/deagglomeration of the drug is not dependant on the air flow rate, patients can be taught to inhale slowly, unlike most dry powder inhalers, thus reducing unwanted drug impaction on the back of their throats.

Generally, the medicament aerosolization/deagglomeration means causes release of medicament from the dose source and disintegration of particle agglomerates by mechanical energy input independent of patient effort. The method employed may be any one or more of a number of suitable physical processes, such as impaction or vibration, brushing or scraping, or the use of a gas flow derived from a compressed or liquefied gas supply, or the use of air turbulence generated by a propeller or impeller. The selection of which method is to be employed varies with the medicament source, e.g., capsule, elongate carrier, or powder reservoir and transfer member. Accordingly, we shall illustrate the invention with reference to the use of an elongate carrier, although the general principles may be applied to inhalers using capsules, transfer members, etc.

The medicament release means serves to weaken the binding of the medicament particles to the carrier and disintegrates particle agglomerates by mechanical effort, e.g., impaction, vibration, gas flow etc., or electrostatically. Mechanical deagglomeration/aerosolization energy input may be achieved by:

(i) impaction means, e.g., one or more spring biased striking hammers having one or more impactions upon the exposed section of carrier;

(ii) brushing or scraping means having rotary or reciprocal motion upon the exposed section of carrier, e.g., spring charged or electrically driven rotary elements having projecting bristles or flaps; dragging the carrier across irregularities such as a serrated idler wheel or a surface bearing a plurality of embossed structures or similar surface features, or dragging the carrier over an edge or corner having a small radius of curvature such that the medicament bearing surface is given a sharp convex curvature;

(iii) pressurized gas flowing past, through or impinging upon the carrier, emanating from some compressed or liquefied gas supply;

(iv) vibration means for imparting vibration to the exposed section of carrier, generally in the frequency range 5 to 250,000 Hertz; the vibrations may be derived electrically or piezo-electrically, e.g., using the piezo-electrical properties of polymer $PVDF_2$; electromagnetically, e.g., using an electromagnetic vibrating arm or pin, or mechanically, e.g., using rotating cams or serrated wheels, which may involve rapid revolution of the cam or wheel in contact with the carrier or movement of the carrier across the cam or wheel.

In a further embodiment, alternative vibration means may comprise means for the rapid acceleration of the elongate carrier, preferably from an unexposed storage state, into the chamber followed by a sudden and rapid deceleration preferably to a dead stop to facilitate medicament release. In such an arrangement the loosely bound particles of medicament are given sufficient kinetic energy to effect release and deagglomeration from the carrier as the carrier comes to a rapid halt. In a further embodiment the elongate carrier is maintained as a slackened loop following advancement into the chamber. Upon actuation, tensioning means effects a sudden and rapid straightening of the carrier loop causing particles of medicament to be released and deagglomerated. The loop may be positioned in any orientation relative to the patient port but in a preferred embodiment the center of curvature of the loop is positioned between the carrier and patient port so that the particles of medicament are released towards the patient port when the loop is rapidly straightened.

Medicament release efficiency may be increased when the carrier and/or the medicament particles have an intentional charge by reversing the polarity of the carrier at aerosolization and inhalation.

The deagglomeration/aerosolization means is triggered in response to the patient inhaling in order to avoid the patient having to synchronize inhalation and actuation of the medicament release mechanism. Airflow detection may conveniently be accomplished by means of a movable vane positioned within the chamber or patient port, motion of the vane causing actuation of the release mechanism, although, any suitable flow sensor able to detect a developing air stream may be used. The vane may be spring biased to return to a home position. Such a vane may also be constructed to prevent a patient exhaling through the device and/or preventing exhaled air from reaching the stored medicament thereby avoiding any problems associated with moisture ingress and agglomeration. Other such sealing means may also be employed.

A control system is included which activates the aerosolization/deagglomeration mechanism in response to the detection of a developing air stream through the device. The control system may be an electrical or mechanical linkage between the flow sensor and means for aerosolization, the selection of which is dependent on the type of flow sensor and the type of aerosolization/deagglomeration mechanism to be employed. For example, in a device having a movable vane for detection purposes, displacement of the same may effect closure of a microswitch or reed switch, thereby completing a circuit including a battery to power an electric motor turning, for example, a propeller or powering a solenoid buzzer. Alternatively vane displacement may effect release of a simple catch restraining a spring loaded striking hammer from impacting with a carrier or transfer member.

Suitable medicaments for use in the invention include any drug or drugs which may be administered by inhalation and which is either a solid or may be incorporated in a solid carrier. Suitable drugs include those for the treatment of respiratory disorders, e.g., bronchodilators, corticosteroids and drugs for the prophylaxis of asthma. Other drugs such as anorectics, anti-depressants, anti-hypertensive agents, antineoplastic agents, anti-cholinergic agents, dopaminergic agents, narcotic analgesics, beta-adrenergic blocking agents, prostoglandins, sympathomimetics, tranquilizers, steroids, vitamins and sex hormones may be employed.

Exemplary drugs include:

Salbutamol, Terbutaline, Rimiterol, Fentanyl, Fenoterol, Pirbuterol, Reproterol, Adrenaline, Isoprenaline, Ociprenaline, Ipratropium, Beclomethasone, Betamethasone, Budesonide, Disodium Cromoglycate, Nedocromil Sodium, Ergotamine, Salmeterol, Fluticasone, Formoterol, Insulin, Atropine, Prednisolone, Benzphetamine, Chlorphentermine, Amitriptyline, Imipramine, Cloridine, Actinomycin C, Bromocriptine, Buprenorphine, Propranolol, Lacicortone, Hydrocortisone, Fluocinolone, Triamcinclone, Dinoprost, Xylometazoline, Diazepam, Lorazepam, Folic acid, Nicotinamide, Clenbuterol, Bitolterol, Ethinyloestradiol and Levenorgestrel. Drugs may be formulated as a free base, one or more pharmaceutically acceptable salts or a mixture thereof.

The powdered medicament may be finely micronized by repeated step wise millings or a closed loop milling system and preferably is in the particle size range of 1 to 10 µm. The medicament may comprise one or more drugs, having one or more particular forms and may include one or more physiologically acceptable or inert excipients. The medicament particles may possess a coating comprising a surfactant, such as a perfluorinated surfactant or other surfactants such as Span 85, oleic acid, lecithins.

BRIEF DESCRIPTION OF THE DRAWINGS

The invention will now be described with reference to the accompanying drawings in which;

FIG. 3a is a front view, FIG. 3b a rear view and FIG. 3c a ventral view of the device exterior. FIG. 3d is a transverse section through the inhaler along the axis A—A.

FIGS. 4a and 4b illustrate an inhaler of the present invention having a battery powered revolving brush for deagglomerating/aerosolizing medicament.

FIG. 5 is a section through an inhaler in accordance with the present invention having battery powered vibration means for deagglomeration/aerosolization.

FIG. 6a is a section through the device in closed format; FIG. 6b is a section through the device flow sensor during patient inhalation and FIG. 6c is a section through the device in open format at medicament aerosolization.

DETAILED DESCRIPTION

Figure 1:
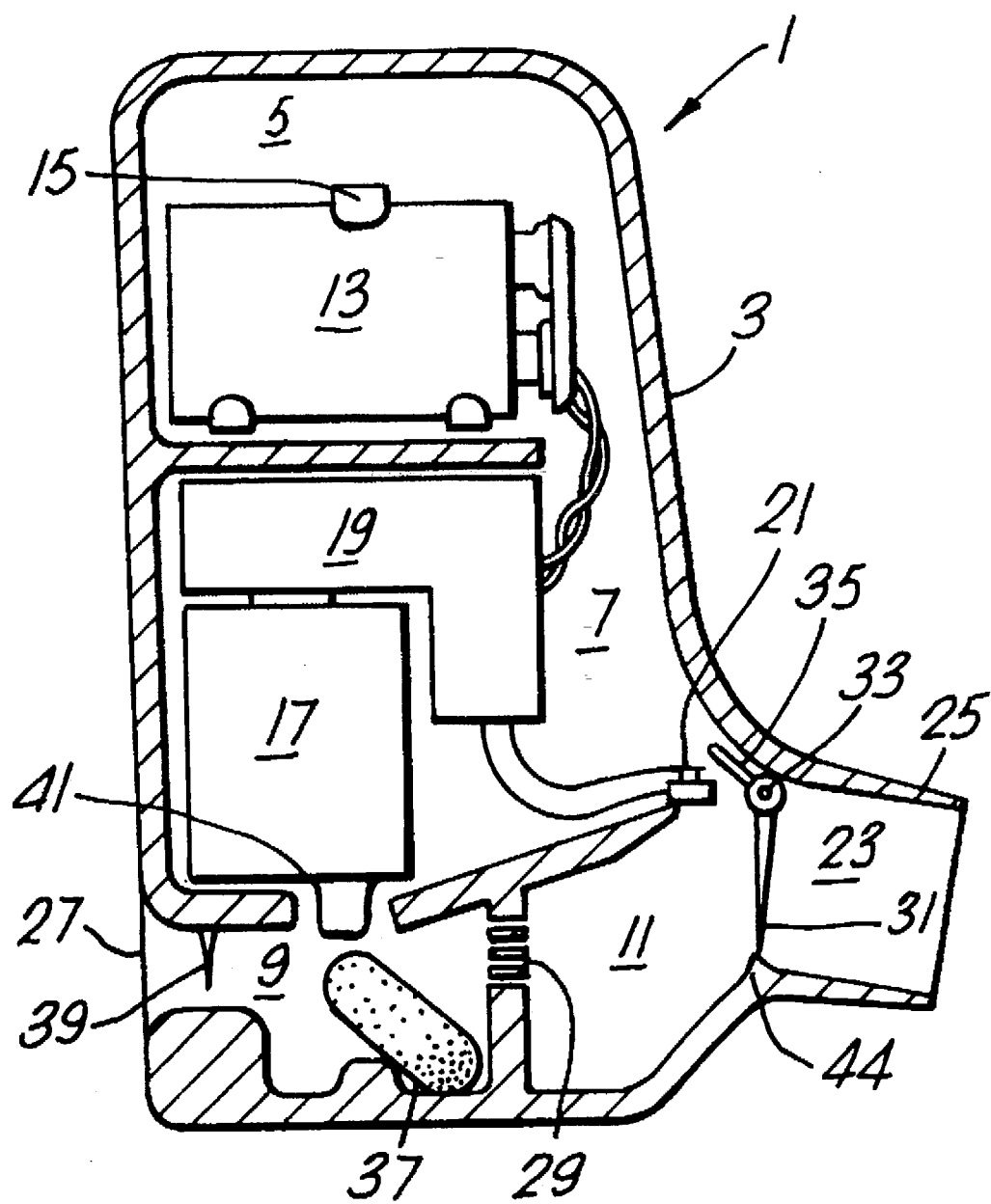
FIG. 1 is a section through an inhaler in accordance with the present invention having battery powered vibration means for deagglomeration/aerosolization.
Figure 2:
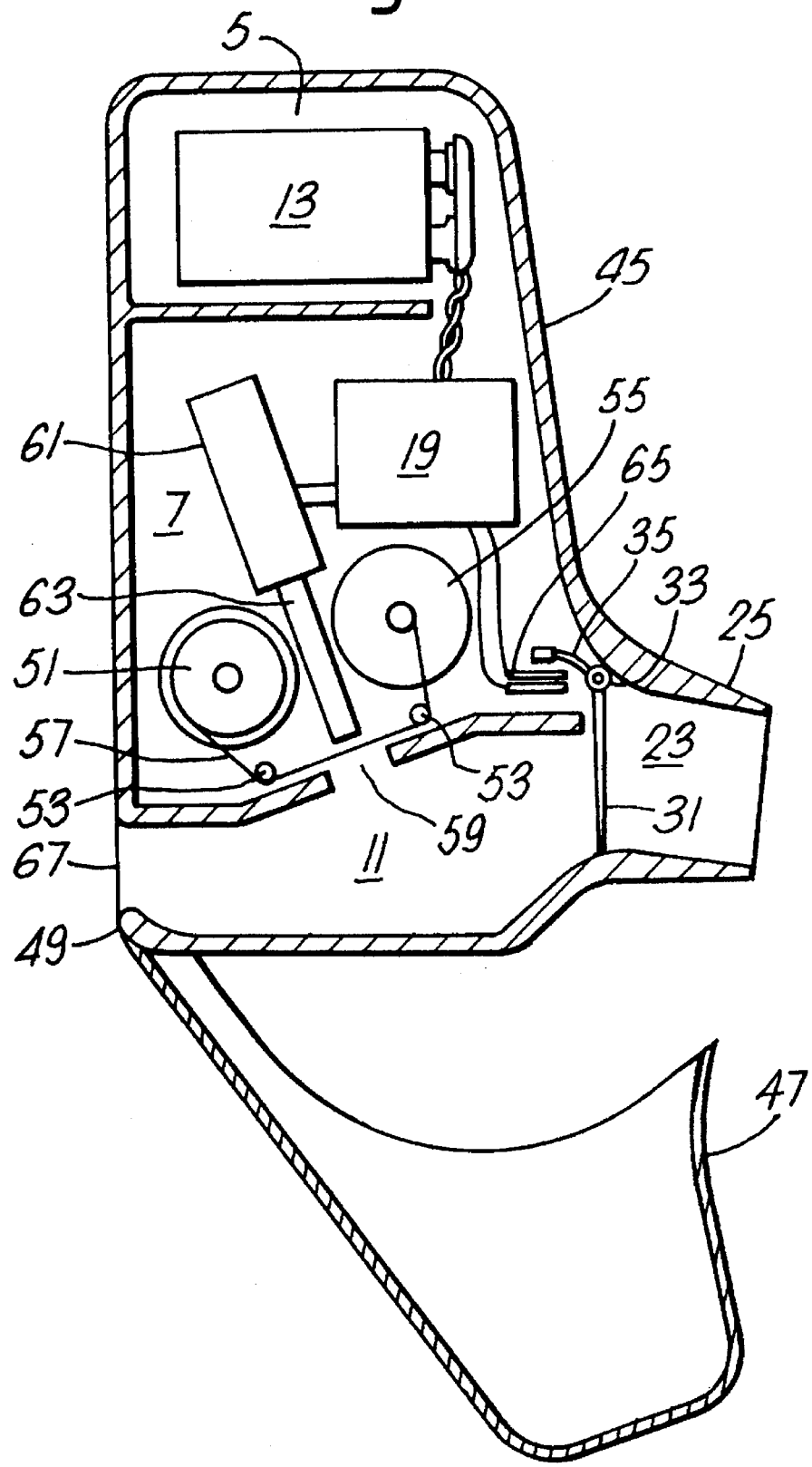
FIG. 2 is a section through an inhaler in accordance with the present invention having battery powered impaction means for deagglomeration/aerosolization.
Figure 3A:
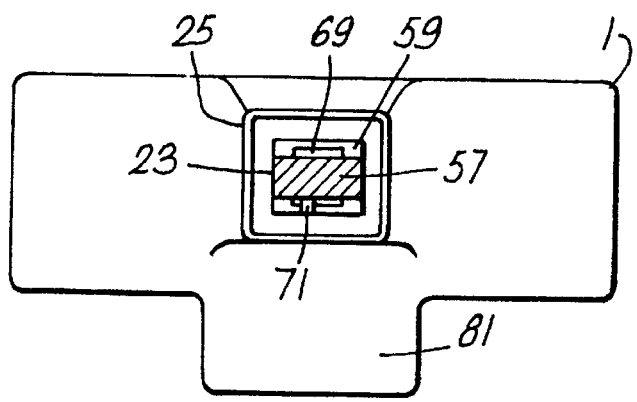
FIGS. 3a to 3d illustrate an inhaler of the present invention having spring loaded impaction means for deagglomeration/aerosolization.
Figure 3B:
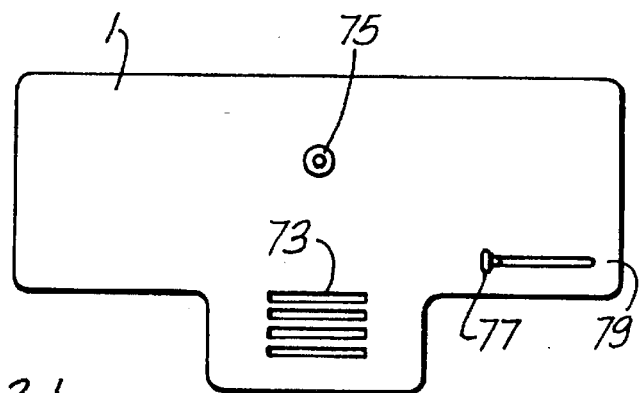
Figure 3C:
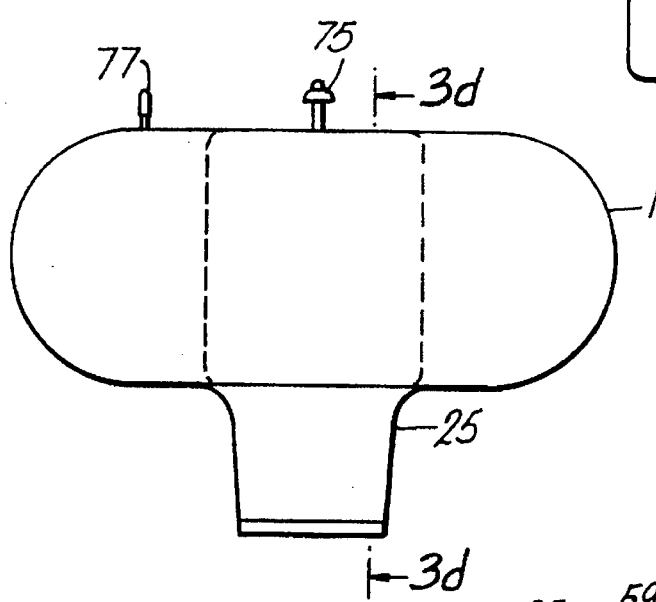
Figure 3D:
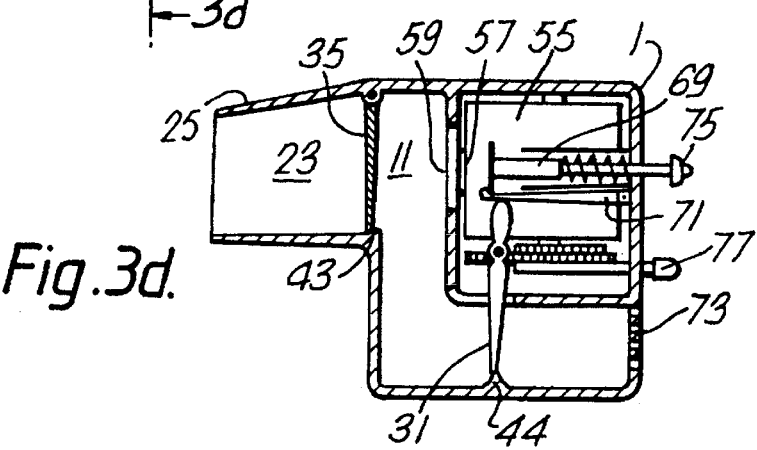

Referring to FIG. 1, an inhalation device (1), for use with powdered medicament enclosed in a rupturable capsule comprises a housing (3) defining interconnecting compartments (5) and (7), capsule receiving enclosure (9) and aerosolization chamber (11). Compartment (5) contains a battery (13) mounted in securing lugs (15) and may be accessed by the patient to replace an exhausted cell. Compartment (7) contains a solenoid-type vibrator (17) in electrical communication with control mechanism (19) and microswitch (21), and completing an electric circuit with battery (13). When the device is not in use microswitch (21) is open, such that the aforementioned circuit is incomplete, thereby preventing vibrator actuation.

Aerosolization chamber (11) communicates with patient port (23) provided with a mouthpiece (25), although the device may be fitted with a nasal adaptor (not shown) or alternatively, the device may be supplied with both. Enclosure (9) communicates with the exterior atmosphere through portal (27) and aerosolization chamber (11) through integral air vents (29), such that an air flow may be generated through the device from the exterior atmosphere by patient inhalation at (23). Vane (31) is pivotally mounted about (33) and is capable of being displaced when an air flow is generated by patient inhalation through the device. Displacement of vane (31) causes an interaction between vane member (35) and microswitch (21), to transiently close switch (21), thereby completing the circuit described above and actuating vibrator (17). Vane member (35) also serves to prevent vane (31) from rotating fully out of patient port (23). The vane is spring biased to return to the home position upon halting of patient air flow causing microswitch (21) to re-open and thereby interrupting the circuit.

In use, a patient inserts a capsule (37) into portal (27) provided with one or more cutting or piercing members (39), such that capsule integrity is destroyed during insertion. Alternatively, the patient may manually rupture the capsule prior to insertion. Enclosure (9) is suitably configured so that the capsule rests in close proximity to the plunger rod (41) of vibrator (17). Vibration of the plunger rod against the capsule upon vibrator actuation causes deagglomeration and release of medicament particles of respirable size from the capsule, whereupon they are entrained into the developing air stream. Vane (31) ensures unidirectional flow of air from the exterior atmosphere via portal (27) to patient port (4) by being displaceable in the forward direction only. Movement in the reverse direction upon patient inhalation is prevented by stop (44). Compartments (5) and (7) may be substantially sealed from enclosure (9) and chamber (11), with the exception of the communication required for operation of both buzzer and vane, to prevent the ingress of powdered medicament which may deleteriously affect device operation.

Referring to FIG. 2, an inhalation device suitable for use with a pre-loaded elongate medicament carrier comprises a housing having a body portion (45) and cover (47) pivoted about (49) and movable between an open position (as shown) and a closed position. While the device is not in use, the cover minimizes the contamination resulting from dirt or moisture ingress. Body portion (45) defines interconnecting compartments (5) and (7) and an aerosolization chamber (11). Compartment (7) contains integral carrier storage spool (51), carrier-engaging guide rollers (53) and integral carrier take-up spool (55), such that carrier (57) may be sequentially advanced across an exposure frame (59) in communication with the aerosolization chamber. Dose advancement means are not shown, but may comprise mounting the take-up spool on a drive shaft extending through the housing, which may be manually turned with the aid of a knurled knob. Alternatively, a suitable gear train may be connected to the take-up spool and a recessed dose advancement wheel or lever mounted in the housing to affect dose advancement. Compartment (7) also contains control mechanism (19), deagglomeration/aerosolization means comprising a solenoid (61) and striking hammer (63) and reed switch (65) completing an electric circuit with battery (13). When the device is not in use, reed switch (65) is open, such that the aforementioned circuit is incomplete, thereby preventing solenoid actuation.

In use, an unexposed portion of carrier (57) is advanced to the exposure frame by the patient before displacement of cover (47) and inhalation through mouthpiece (25). An air flow is generated through the device via vent (67) to patient port (23). Displacement of vane (31) as described in FIG. 1 causes member (35) to transiently close reed switch (65), such that the control mechanism (19) selectively activates solenoid (61) causing hammer (63) to impact upon the exposed section of the carrier. Impaction of the hammer with carrier (57) releases medicament particles of respirable size into aerosolization chamber (11), whereupon they are entrained into the developing air stream as the patient inspires.

Referring to FIG. 3*a*, a front view of an inhaler having indirect breath actuation of impaction means is illustrated. Vane (85), explained hereinafter, has been omitted to illustrate how the exposure frame (59) presented to the patient by insertion of mouthpiece (25) into the buccal cavity, defines the exposed area of elongate carrier (57). Striking hammer (69) is held in an armed position by catch (71) and is released by the detection of an air flow through the device.

FIG. 3*b* depicts a rear view of the inhaler of FIG. 3*a* and illustrates the position of air vents (73), striking hammer arming rod (75) and dose advancement lever (77) recessed in slot (79).

FIG. 3*c* depicts a plan view of the inhaler of FIG. 3*a*.

FIG. 3*d* depicts a section through the inhaler along the axis A—A. The inhaler comprises: a housing (1) having an extension (81), for purposes of indirect breath actuation with integral air vents (73), the housing defining an aerosolization chamber (11) in communication with patient port (23) and air vents (73). Carrier (57) is taken up by spool (55). Carrier storage means are not shown but typically would also be a spool.

Unexposed carrier (57) is sequentially advanced across exposure frame (59) by recessed lever (77) driving a suitable gear train (83) turning spool (55). Striking hammer (69) is-primed by the patient prior to inhalation by retracting spring biased rod (75) until catch (71) is engaged.

Vane (31) is capable of being displaced when an air flow is generated by patient inhalation through the device. The vane is spring biased (not shown) to return to the displaceable home position when the air flow is halted. Displacement of the vane (31) produces an interaction with catch (71) to release the striking hammer (69). Impaction of the hammer with carrier (57) releases medicament particles of respirable size into aerosolization chamber (11), whereupon they are entrained into the developing air stream as the patient inspires.

Vane (85) ensures unidirectional flow of air from the exterior atmosphere, via air vents (73) to patient port (23), by being displaceable in the forward direction only. Movement in the reverse direction upon patient exhalation is prevented by stop (43).

In a modification (not shown) the vanes (31) and (85) may be replaced by a single vane.

Referring to FIGS. 4*a* and 4*b*, an inhaler having both integral carrier storage spool (51), take up spool (55) and brushing/scraping means for aerosolization is illustrated. Carrier (57) is sequentially advanced across the carrier support (87) in contact with a spring powered or electrically driven (not shown) rotary brush (89).

Indirect breath actuation is provided by the displacement of vane (31) by a developing air stream during patient inspiration, thereby completing an electrical circuit containing a battery and a motor (not shown) to drive rotary brush (89), or alternatively allowing a tensioned spring mechanism (not shown) to revolve the brush.

FIG. 5 illustrates an inhaler of re-usable format comprising a disposable cassette (91) with part of the housing and disposable cassette cut away. The cut away illustrates the relative position of carrier storage spool (52) and carrier take up spool (56) within said cassette to the gear train driving carrier advancement (83). Spools (52, 56) are engaged respectively upon cassette insertion by spindles (only spindle (52a) for the storage spool is shown). An inhaler of disposable format may be produced by replacing cassette (91) with integral spools (51, 55) not shown. Sequential advancement of fresh carrier (57) to exposure frame (59) is completed by a recessed dose advance wheel (93) engaging gear train (83) and revolving take up spool (56). Solenoid buzzer (17) is activated by completion of a circuit containing a battery cell (not shown). This may be achieved by the incorporation of a displaceable vane (not shown) as described in FIGS. 1 to 4. Vibrating head (41) contacting the carrier at exposure frame (59) causes medicament to be released from the carrier, where it may be entrained by the patients inspiratory efforts.

Figure 6A:
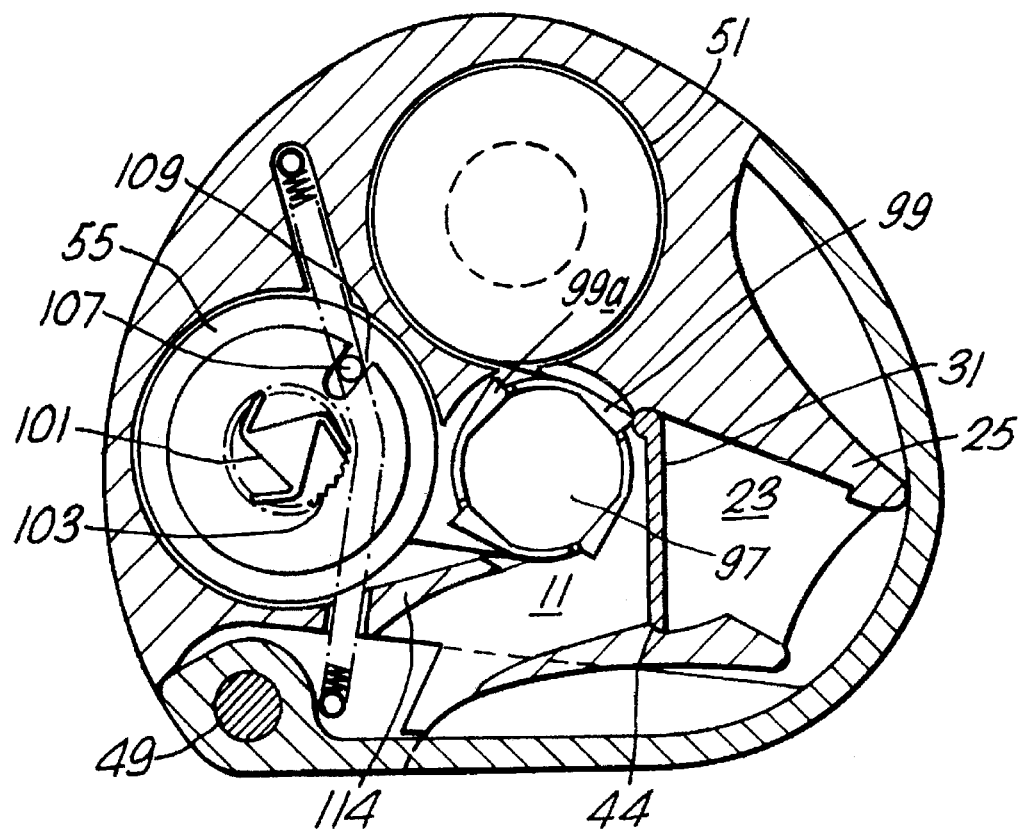
FIGS. 6a to 6c illustrate an inhaler of the present invention having scraping means for medicament deagglomeration/aerosolization and a housing assembly having a cover.
Figure 6B:
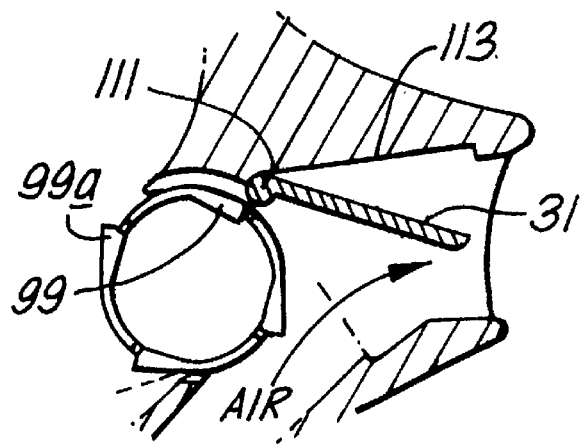
Figure 6C:
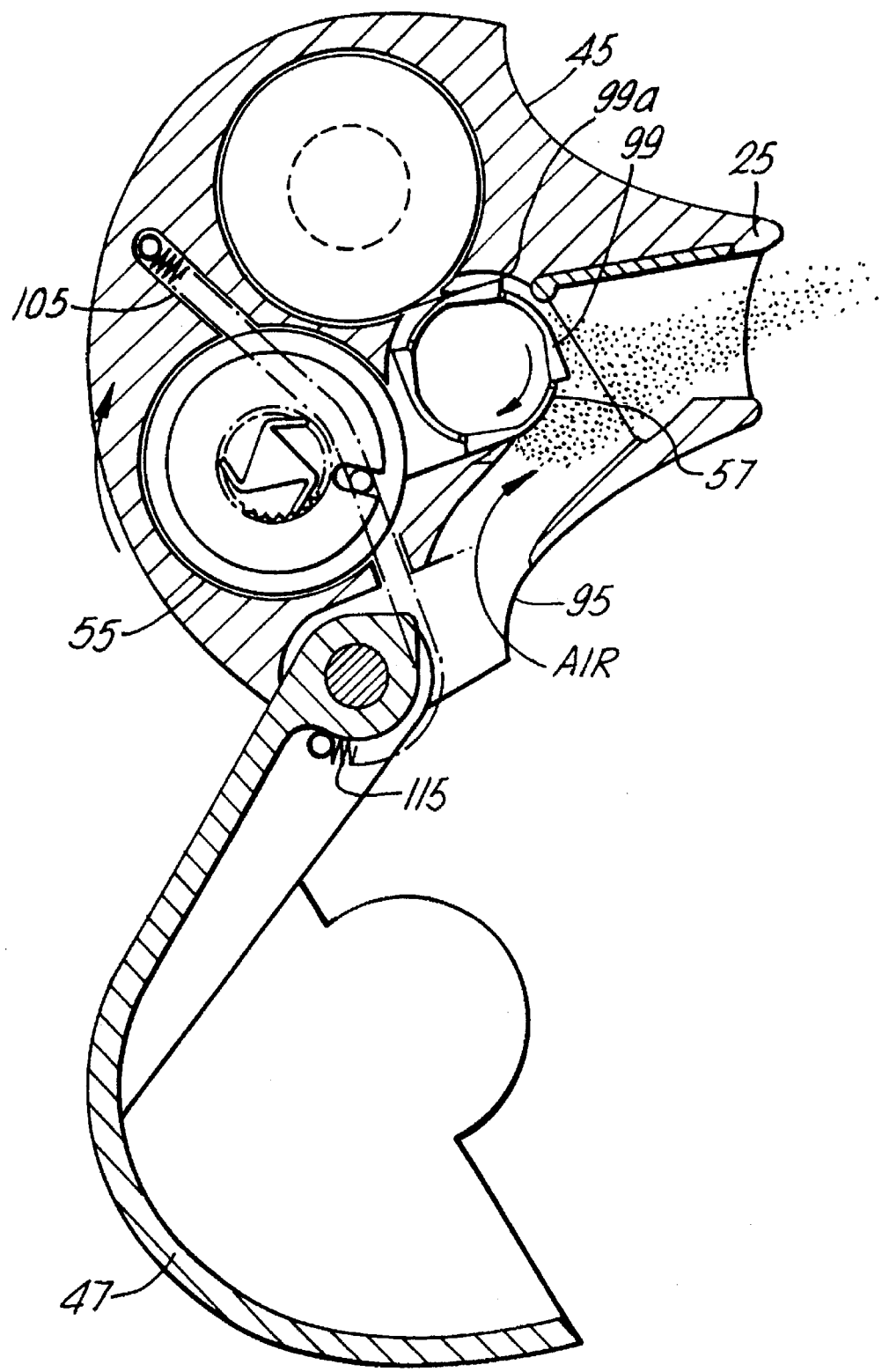

FIGS. 6a to 6c illustrate sections through an inhaler having a housing comprising a body portion (45) and a cover (47) pivotally mounted at (49) movable between a closed format shown in FIG. 6a and an open format shown in FIG. 6c. The inhaler is maintained in a closed position whilst not in use providing a compact, convenient shape minimizing contamination from dirt, moisture ingress etc.

The housing has one or more integral air vents (95), which are exposed when the device is in the open format, and defines an aerosolization chamber (11) in communication with a patient port (23), having a mouthpiece adaptor (25). Within the chamber are integral carrier storage spool (51), idler (97) having four lobed catches (99) of equal dimension, and carrier take up spool (55) having a pawl (101) and ratchet (103) allowing unidirectional rotation of the spool (indicated by the arrow of FIG. 6*c*) when idler catch (99) is released.

In an alternative embodiment (not shown) the carrier storage spool (51) or both spools may be incorporated into a disposable cassette and the housing assembly is modified to receive the cassette and allow replacement thereof.

The device is cocked for use by fully opening the cover (47) causing tensioning of the drive spring (115) which acts on drive peg (107) which is engaged in a slot (109) in carrier take up spool (55). Rotation of take up spool (55) by the drive peg (107) is prevented by the engagement of displaceable idler catch (99) with vane pivot axle (111). Opening the device exposes the patient port and mouthpiece adaptor to the patient.

FIG. 6*b* illustrates the actuation of the device by a developing airstream as the patient inhales. Vane (31) provides indirect breath actuation means and may additionally prevent through device exhalation by the patient. The vane is pivoted so as to be displaceable when an airflow is generated through the device from the exterior via vents (95) to the patient port (23). Unidirectional displacement of vane (31) is provided by the vane engaging stop (43). The vane may have a width equal to the patient port such that upon exhalation the vane sealing contacts stop (43) preventing the ingress of moist, exhaled air. In the home (non-displaced) position the vane engages catch (99) preventing carrier advance. Inhalation displaces vane (31) into recess (113) whilst displacing and freeing idler catch (99) from engagement by vane pivot axle (111) and allowing idler (97) to complete the cycle until the following catch (99*a*) re-engages the vane pivot axle. The curvature of each catch aids the stepwise engagement of vane pivot axle (111) to define dosage lengths of carrier.

Referring to FIG. 6*c*, medicament is removed from the carrier by a combination of acceleration/deceleration impaction and the action of scraper (114). With idler (97) free from interruption the tensioned spool (55) rapidly winds up carrier (57) under the influence of drive spring (105) moving drive peg (107) until the passage of idler (97) is abruptly halted by the next catch (99*a*) re-engaging pivot axle (111). The resulting momentum of medicament particles, the impaction due to the arresting of carrier velocity and the resulting vibration of the carrier aid medicament removal. The curvature of idler (97) bends the carrier with drug coating outwards as each new unexposed section is indexed onto the idler (97) and exposed to the airstream, thereby easing the release of powder. Scraper (114) aids the release of medicament by contacting the exposed area of carrier prior to take up and mechanically displaces the medicament particles. After use the device is returned to the closed format by the patient, the drive peg (107) being returned to its original position under the influence of return spring (105).

FIGS. 7*a* and 7*b* illustrate alternative embodiments of a variation of the inhaler illustrated in FIGS. 6*a* to 6*c*. Both devices are shown in the inactive closed format.

FIG. 7*a* illustrates an inhaler having a spring biased cam follower comprising a spring (117), biasing wheel mounting (119) and cam follower wheel (121). Cam follower wheel (121) engages and travels the surface of cam (123) during cam rotation. Cam (123) has an essentially square cross section and abuts idler (125) having four displaceable catches (127) of equal dimensions. Vane (31) provides indirect breath actuation means and may form a one way valve preventing exhalation through the inhaler. The device is cocked as described previously for FIGS. 6*a* to 6*c*, movement of the carrier being prevented by engagement of catch (127) with vane pivot axle (111).

When the patient inhales, vane (31) is displaced into recess (113). Idler (125) is no longer blocked allowing carrier (57) to be drawn onto take up spool (55). As the carrier is taken up, passage of cam follower wheel on the surface of cam (123) for the first 45° of rotation compresses spring (117) such that during the second part of the cycle (a further 45° rotation), cam follower wheel (121) causes the cam to rotate faster than take up spool (55). A loop of carrier (not shown) develops until idler (125) rotation is prevented by engagement of following catch (127*a*) with vane pivot axle (111). Subsequently the loop of carrier is snapped tight by take up spool (55) causing release of medicament into the airstream.

FIG. 7*b* illustrates an inhaler having a cam assembly comprising a central cam (129) of essentially square cross section abutting a guide wheel (131) bearing carrier (57) and an interrupter wheel (133) having, at the four compass positions, circular elements (135) of equal dimensions and freely rotatable about an axis; a spring biased cam follower comprising a spring (117) biasing wheel mounting (119), supporting cam follower wheel (121) and an interrupter assembly comprising a rocker arm (139) pivoting about pivot point (155) and bearing a peg (143) and a catch (145) having a spring leaf (147). Catch (145) is able to pivot about pivot point (141). Cam follower wheel (121) engages and travels the surface of central cam (129) during rotation of the cam assembly. Rocker arm (139) is biased by the action of a weak spring (149), fixed between peg (151) of body (1) and slot (153), such that the rocker arm nose (155) stepwise engages circular elements (135) at every 90° rotation of the cam assembly.

The device depicted illustrates alternative embodiments to the format of the drive (115) and return (105) springs described previously and the idler/ratchet mechanism ensuring unidirectional rotation of carrier take up spool (55).

Figure 7A:
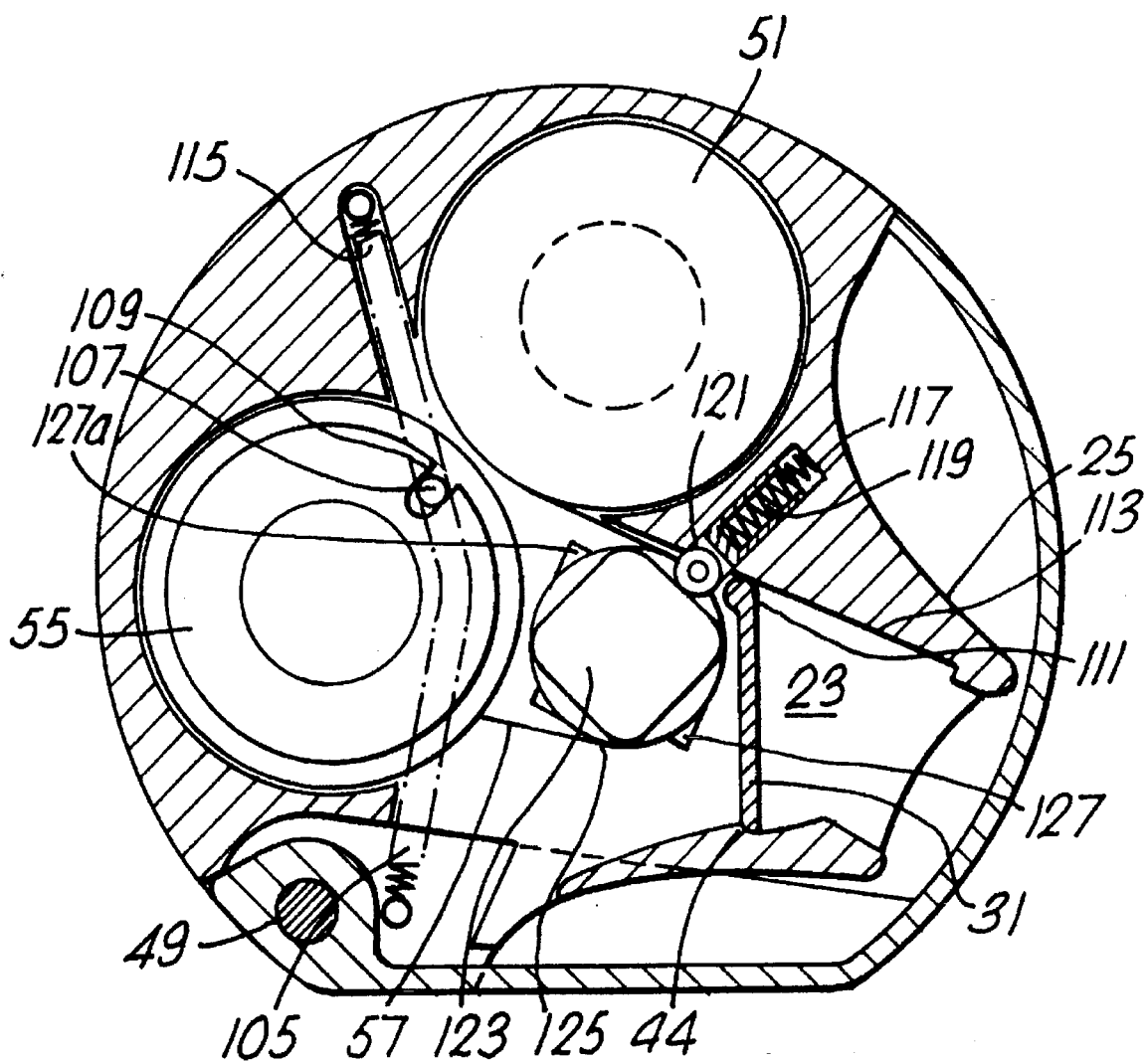
FIGS. 7a and 7b illustrate sections through alternative inhalers of the present invention.
Figure 7B:
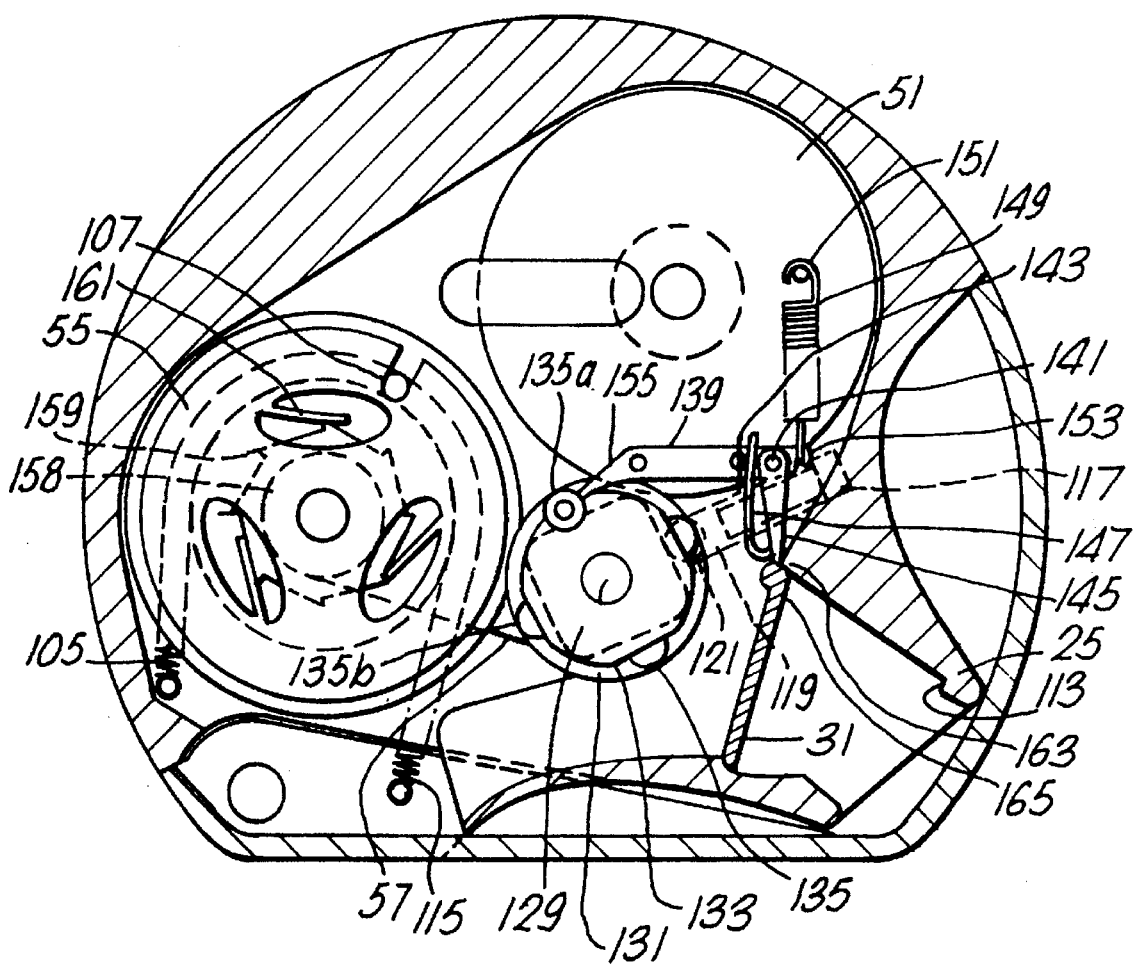

In use, the device is cocked as described for FIGS. 6a, 6c and 7a by opening of the cover, whereby drive peg (107) is tensioned by the activity of drive spring (115). Unidirectional (clockwise) rotation of take up spool (55) is effected by the action of spindle (158) having a series of stepped projections (159) engaging the spring leaves (161) of the spool in the reverse (anti-clockwise) direction. Tensioned drive peg (107) imparts a slight rotation to take up spool (55) causing tightening of any slack carrier (57). Rotation of the take up spool (55) is prevented by the engagement of rocker arm (139) to the interrupter wheel (133), but the rocker nose (155) is caused to be displaced slightly on the circular element (135a). The slight lift imparted to the rocker nose (155) in a reciprocal motion about the pivot causes catch (145) to engage the curved surface (163). The curved surface (163) directs catch (145) to rest upon vane (31). Vane (31) provides indirect breath actuation.

Patient inhalation through mouthpiece adaptor (25) displaces vane (31) into recess (113) as described previously. Rotation of the vane about pivot point (165.) causes the displacement of catch (145). As catch (145) is displaced from a blocking to a non-blocking position, rocker arm (139) is lifted by interrupter element (135a) thus allowing rotation of the cam assembly. Rocker arm (139) is maintained in contact with the surface of interrupter wheel (133) by spring (149) so that it contacts the following interrupter element (135b). This provides a stepwise mechanism (every 90° rotation of the cam assembly) for carrier exposure. Cooperation of central cam (129) and spring biased cam follower cause a loop of carrier to be formed which is snapped tight causing release of medicament particles as described in FIG. 7a.

Other examples of devices in accordance with the invention are disclosed in PCT Application No. US90/02412 of even date based on British Patent Application No. 8909891.

We claim:

1. A dry powder inhaler comprising a housing defining a chamber for receiving a dose of powdered medicament in communication with a patient port in the form of a mouthpiece or nasal adapter, the inhaler additionally comprising:

deagglomeration/aerosolisation means to deagglomerate and/or assist aerosolization of a dose of powdered medicament, which means is operable by a patient-independent energy output source, detection means to detect patient inspiration through the patient port, and, control means to actuate said deagglomeration/aerosolisation means in response to detection of patient inspiration by said detection means.

2. A dry powder inhaler as claimed in claim 1 further comprising a dose of powdered medicament and an elongate carrier, wherein the dose of powdered medicament is carried upon said elongate carrier, and in which the inhaler is constructed and arranged such that areas of said carrier, of a predetermined size, are sequentially exposed within said chamber.

3. A dry powder inhaler as claimed in claim 2 in which a the elongate carrier is preloaded with a medicament and is in the form of a tape.

4. A dry powder inhaler as claimed in claim 3 in which the deagglomeration/aerosolization means is selected from the group consisting of (i) means for brushing or scraping an exposed area of the tape or powder transfer member by rotary or reciprocal motion, (ii) means for dragging the tape or powder transfer member across a surface having irregularities, or an edge or corner having a small radius such that the surface of the elongate carrier material bearing powdered medicament is given a sharp convex curvature, (iii) means causing an unexposed area of the elongate carrier or powder transfer member to advance rapidly into the chamber during inhalation by the patient and come to an abrupt halt causing medicament release, and, (iv) means causing an unexposed length of elongate carrier to take the form of a slackened loop, which upon inhalation is rapidly straightened to cause medicament release.

5. A dry powder inhaler as claimed in claim 1 additionally comprising a storage reservoir for powdered medicament and a powder transfer member, and in which the inhaler is constructed and arranged such that the transfer member passes through or past the storage reservoir so that a controlled quantity of medicament is coated onto the surface of said member before passage into said chamber.

6. A dry powder inhaler as claimed in claim 1 in which the dose of powdered medicament is enclosed in a rupturable capsule and the inhaler is adapted to receive said capsule and comprises means for breaching the capsule.

7. A dry powder inhaler as claimed in claim 1 in which the patient-independent energy output is derived from a source selected from the group consisting of a spring, or other biasable resilient energy storage means, a battery and a source of compressed or liquefied gas.

8. A dry powder inhaler as claimed in claim 7 in which the means for impacting or striking is selected from the group consisting of a biased hammer arrangement and a solenoid and plunger rod.

9. A dry powder inhaler as claimed in claim 1 in which the deagglomeration/aerosolization means comprises means selected from the group consisting of impacting, striking and vibrating the dose of powdered medicament.

10. A dry powder inhaler as claimed in claim 9 in which said deagglomeration/aerosolization means produces vibrations in the frequency of from 5 to 250,000 Hz and is selected from the group consisting of an electrical, piezoelectric, electromagnetic and mechanical means.

11. A dry powder inhaler as claimed in claim 9 in which the means for vibrating is selected from the group consisting of a solenoid-type vibrator, rotating cams and serrated wheels.

12. A dry powder inhaler as claimed in claim 1 in which the deagglomeration/aerosolisation means comprises a propeller or an impeller generating a flow of air turbulence causing medicament release.

13. A dry powder inhaler as claimed in claim 1 in which the detection means comprises a movable vane, the vane being movable upon inhalation through the patient port to trigger said control means to actuate said deagglomeration/aerosolisation means.

14. A dry powder inhaler as claimed in claim 1 which further comprises a dose of powdered medicament having a particle size in the range of 1 to 10 um and comprises one or more drags selected from the group consisting of bronchodilators, corticosteroids, anorectics, anti-depressants, anti-hypertensive agents, anti-neoplastic agents, anti-cholinergic agents, dopaminergic agents, narcotic analgesics, β-adrenergic blocking agents, prostoglandins, sympathomimetics, tranquilizers, steroids, proteins, peptides, vitamins, sex hormones and drugs for the phophylaxis of asthma.

15. A dry powder inhaler as claimed in claim 14 in which the medicament is selected from the group consisting of Salbutamol, Terbutaline, Rimiterol, Fentanyl, Fenoterol, Pirbuterol, Reproterol, Adrenaline, Isoprenaline, Ociprenaline, Ipratropium, Beclomethasone, Betamethasone, Budesonide, Disodium Cromoglycate, Nedocromil Sodium, Ergotamine, Salmeterol, Fluticasone, Formoterol, Insulin, Atropine, Preunisolone, Benzphetamine, Chlorphentermine, Amitriptyline, Imipramine, Chloridine, Actinomycin C, Bromocriptine, Buprenorphone, Propranolol, Lacicortone, Hydrocortisone, Fluocinolone, Trimcincione, Dinoprost, Xylometazoline, Diazepam, Lorazepam, Folic acid, Nicotimamide, Clenbuterol, Bitolterol, Ethinyloestradiol and Levenorgestrel and pharmaceutically acceptable salts thereof.

* * * * *

UNITED STATES PATENT AND TRADEMARK OFFICE
CERTIFICATE OF CORRECTION

PATENT NO. : 5,655,523
DATED : August 12, 1997
INVENTOR(S) : Peter D. Hodson, David K. Smith and Anthony C.L. Wass It is certified that error appears in the above-identified patent and that said Letters Patent is hereby corrected as shown below:

Column 18,
Claim 8, "7" should read --9--.
Claim 14, "um" should read --µm-- and "drags" should read -- drugs --.

Signed and Sealed this

Seventeenth Day of July, 2001

Attest:

Attesting Officer

NICHOLAS P. GODICI
Acting Director of the United States Patent and Trademark Office